(12) United States Patent
Lai et al.

(10) Patent No.: US 11,666,874 B2
(45) Date of Patent: Jun. 6, 2023

(54) METHODS AND APPARATUS FOR VARIABLE EMULSIFICATION

(71) Applicant: Massachusetts Institute of Technology, Cambridge, MA (US)

(72) Inventors: David Lai, Philadelphia, PA (US); Filippos Touriomousis, Cambridge, MA (US); Andreas Mershin, Arlington, MA (US); Neil Gershenfeld, Cambridge, MA (US)

(73) Assignees: Glaxosmithkline Intellectual Property Deveelopment Limited, Brentford (GB); Massachusetts Institute of Technology, Cambridge, MA (US)

( * ) Notice: Subject to any disclaimer, the term of this patent is extended or adjusted under 35 U.S.C. 154(b) by 1124 days.

(21) Appl. No.: 16/052,705

(22) Filed: Aug. 2, 2018

(65) Prior Publication Data
US 2019/0184351 A1    Jun. 20, 2019

Related U.S. Application Data

(60) Provisional application No. 62/598,734, filed on Dec. 14, 2017.

(51) Int. Cl.
*B01F 23/41* (2022.01)
*B01F 33/3011* (2022.01)
(Continued)

(52) U.S. Cl.
CPC .......... *B01F 33/3011* (2022.01); *A61K 9/107* (2013.01); *B01F 23/41* (2022.01);
(Continued)

(58) Field of Classification Search
CPC ................ B01F 3/0807; B01F 23/41
(Continued)

(56) References Cited

U.S. PATENT DOCUMENTS 2,132,854 A  *  10/1938  Knott .................... B01F 5/0688
138/42
4,259,021 A  *  3/1981  Goudy, Jr. ............ B01F 5/0609
366/118

(Continued)

*Primary Examiner* — David L Sorkin
(74) *Attorney, Agent, or Firm* — Dunlap Bennett & Ludwig, PLLC

(57) ABSTRACT

The invention comprises a novel modular, generalizable meso-micro-nano-fluidic platform apparatus, design and methodology which in exemplary embodiments may be applied in conjunction with a novel external triggering and automation/feedback loop control mechanism deployed via computer to explore the phase space of single or double emulsification for applications including the encapsulation of hydrophilic active pharmacological ingredients (APIs). End use applications include the mass production of particulate encapsulation of hydrophobic or hydrophilic APIs with automatic or user-supervised feedback methodology to control and discover mass production or per-drug customized settings of interest for the manufacture of novel or extant therapeutics. This invention allows for a process to produce monodispersed particles of varying sizes and may be used to rapidly screen for optimal size for maximal bioavailability of API particles either on lab bench for in vitro dissolution or in vivo studies, and patient-specific handhelds for maximal drug inhalation.

25 Claims, 11 Drawing Sheets

Figure 2A:
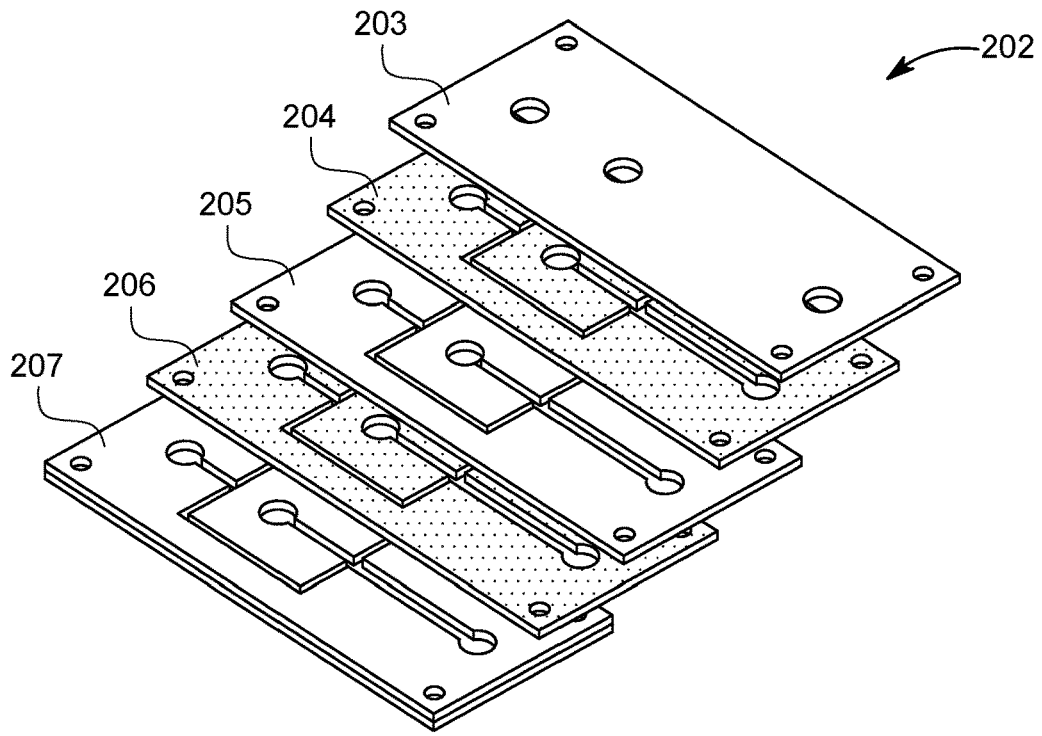

(51) Int. Cl.
*C09D 11/102* (2014.01)
*A61K 9/107* (2006.01)
*B33Y 80/00* (2015.01)
*B01L 3/00* (2006.01)
*B01F 33/81* (2022.01)
*B01F 35/00* (2022.01)
*B01F 35/22* (2022.01)
*B01F 101/22* (2022.01)

(52) U.S. Cl.
CPC ........ *B01F 33/813* (2022.01); *B01F 35/2202* (2022.01); *B01F 35/561* (2022.01); *B01L 3/502784* (2013.01); *B33Y 80/00* (2014.12); *C09D 11/102* (2013.01); *B01F 23/4143* (2022.01); *B01F 2101/22* (2022.01); *B01L 2300/0887* (2013.01)

(58) Field of Classification Search
USPC ...................................................... 366/176.1
See application file for complete search history.

(56) References Cited

U.S. PATENT DOCUMENTS

| | | | | |
|---|---|---|---|---|
| 4,383,769 A * | 5/1983 | Pandolfe | ................ | A01J 11/16 137/1 |
| 4,869,849 A * | 9/1989 | Hirose | ................ | B01F 5/0682 261/78.2 |
| 4,952,067 A * | 8/1990 | Dallas | ................ | B01F 25/4422 99/452 |
| 5,690,763 A * | 11/1997 | Ashmead | ............. | B01F 25/422 422/38 |
| 5,727,618 A * | 3/1998 | Mundinger | ........... | F28F 21/085 257/E23.098 |
| 5,984,519 A * | 11/1999 | Onodera | ................... | B01F 3/12 366/165.2 |
| 6,379,035 B1 * | 4/2002 | Kubo | ..................... | B01F 5/061 366/340 |
| 7,066,641 B2 * | 6/2006 | Honda | ................ | B01F 35/7182 366/DIG. 3 |
| 7,175,335 B2 * | 2/2007 | Furukawa | ............. | B01F 5/0688 366/155.1 |
| 7,374,332 B2 * | 5/2008 | Higashino | ........... | B01F 33/3021 137/602 |
| 7,520,661 B1 * | 4/2009 | Lawson | ................. | B01F 33/30 138/42 |
| 8,042,989 B2 * | 10/2011 | Gordon | ................ | B01F 5/0603 366/176.1 |
| 8,066,955 B2 * | 11/2011 | Pinchot | ................ | B01J 19/0093 422/600 |
| 8,182,132 B2 * | 5/2012 | Nagai | ................ | B01F 13/0059 366/147 |
| 8,231,265 B2 * | 7/2012 | Ozawa | ................ | B01F 25/433 366/337 |
| 10,874,997 B2 * | 12/2020 | Weitz | ..................... | B01F 23/41 |
| 2003/0039169 A1 * | 2/2003 | Ehrfeld | ............. | B01J 19/0093 366/340 |
| 2004/0258601 A1 * | 12/2004 | Matsubara | .......... | B01F 25/3142 502/8 |
| 2005/0092681 A1 * | 5/2005 | Higashino | ........... | B01F 33/3011 366/150.1 |
| 2015/0224457 A1 * | 8/2015 | Schultz | ................ | B01F 13/0059 435/194 |
| 2016/0271610 A1 * | 9/2016 | Foulds | ................ | B01F 23/811 |

* cited by examiner

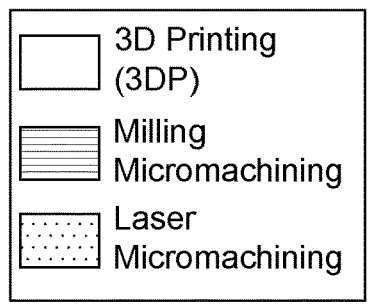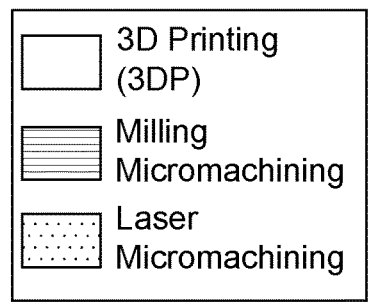
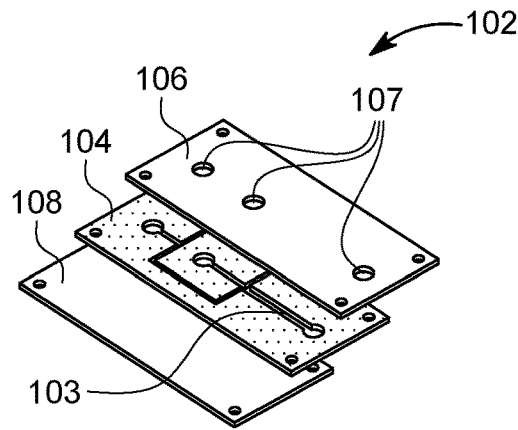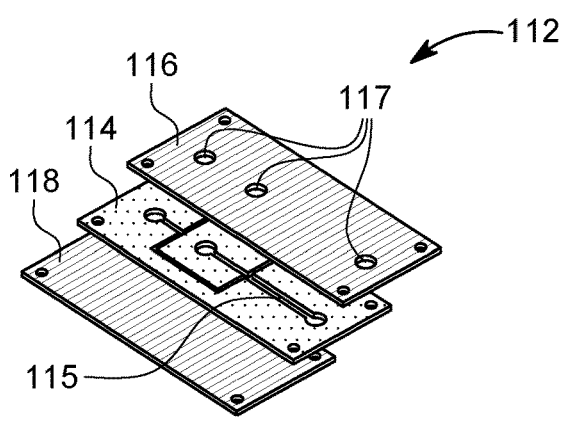
FIG. 1A　　　　　　　　　　FIG. 1B
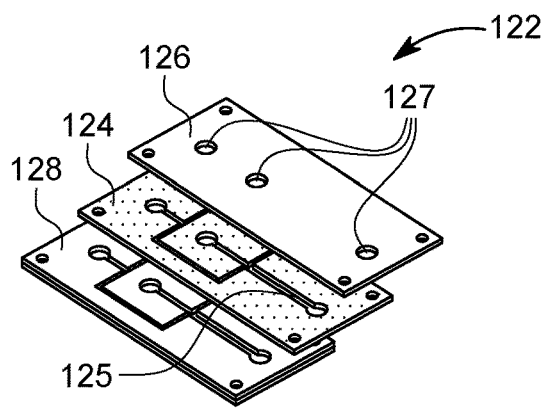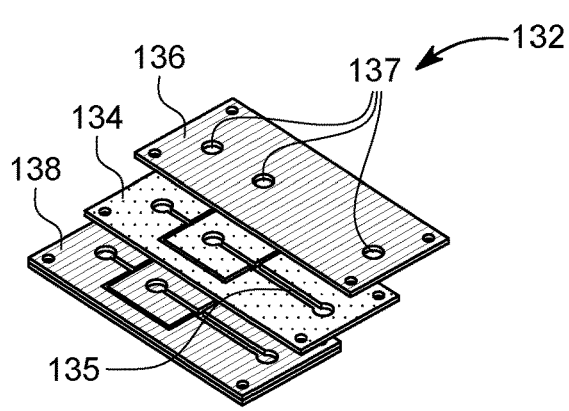
FIG. 1C　　　　　　　　　　FIG. 1D

METHODS AND APPARATUS FOR VARIABLE EMULSIFICATION

This application claims the benefit of U.S. Provisional Application No. 62/598,734, filed Dec. 14, 2017, the entire disclosure of which is herein incorporated by reference.

TECHNICAL FIELD OF THE INVENTION

The invention disclosed herein relates to the fields of:
- high-throughput nano-, micro- and milli-fluidics-based drug manufacturing/packaging inside droplets ("emulsions"),
- hybrid rapid prototyping of such fluidic devices ("emulsifiers") using lamination (sealing/bonding) methods in combination with three-dimensional printing (3DP), laser and milling micromachining methods, and
- in-process continuous and feedback enabled quality control using computer vision methods, machine olfaction methods and in-situ characterization methods.

BACKGROUND OF THE INVENTION

An emulsion is here defined as a mixture of two or more unmixable (immiscible) liquids in the form of a droplet or a particle with the terms being used here interchangeably. Single emulsions are created by dispersing one liquid (dispersed phase) into another liquid (continuous phase). Examples of such emulsions are "water-in-oil emulsions", where water and oil is the dispersed and continuous phase, respectively. The boundary between the dispersed and continuous phases is called the "interface." In exemplary embodiments of the invention the emulsification process is realized by driving the two liquid phases through separate micron- or nanoscale fluidic channels that meet at a certain point. Device geometry and appropriate tuning of flow rate settings in combination with material properties can promote interfacial instabilities for droplet generation. These devices are called hydrodynamic flow focusing fluidic devices and hereafter are referred as emulsifiers.

Drugs consist of two core components: the active pharmaceutical ingredient (API), which is the central biologically active ingredient, and the excipient, here defined as the substance inside the drug formulation that helps deliver the medication. The terms API and "active drug" are used interchangeably in the medical field, and the term active substance may be used for natural products. Excipients are chemically inactive substances, such as for instance a mineral oil. For instance, in treating a headache, acetaminophen is a typical active ingredient, while the liquid in the capsule or the bulk of a pill is the excipient. Bioavailability is herein used to express the quantity of the API that is being delivered, and is actually used to do its therapeutic function. It can be lost in a variety of ways (location, chemical stress, mechanical stress, human error, etc).

Active Pharmaceutical Ingredients (APIs) must often be stabilized as emulsions. During this process a hydrophobic API may be encapsulated in a few or numerous micron diameter particles to prevent rapid degradation, increase bioavailability and/or provide controlled release and the control and generation of these emulsions.

Specifically, mass production of such particles, discovery of optimal conditions and quality control over their size distributions are three aspects of the embodiments described here. Correct formulations of the flow rates of solvent, antisolvent and API for single, double or multiple emulsification are sensitive to hard to precisely control environmental conditions. An additional complication arises from the fact that the optimal size of a particle depends on the API and the mode of administration. And discovering these parameters requires reproducible assays. In addition, the caustic nature of solvents, requires the rapid prototyping of parallelized emulsifiers made from chemically-inert materials outside of cleanroom facilities to lower the cost and expedite the time of investigation. The ability to mass produce emulsions of designed size and low dispersions, as well as reject those that do not pass the quality control criteria and returning to continuous production without interruption, are the focus of the methods and apparatus described here.

Embodiments of the present invention comprise a novel modular, generalizable meso-micro-nano fluidic platform apparatus and design and methodology, which in exemplary embodiments may be applied in conjunction with a novel external triggering and automation/feedback loop control mechanism deployed via PC to explore the phase space of single or double emulsification for applications including the encapsulation of hydrophilic active pharmacological ingredients (APIs). End use applications include the mass production of particulate encapsulation of hydrophobic or hydrophilic APIs with automatic or user-supervised feedback methodology to control and discover mass production or per-drug customized settings of interest for the manufacture of novel or extant therapeutics. This invention allows for a process to produce monodispersed microparticles of varying sizes and may be used to rapidly screen for optimal size for maximal bioavailability of API particles either on lab bench for in vivo dissolution or in vitro animal studies, and potentially even patient-specific handhelds for maximal drug inhalation for respiratory.

SUMMARY OF THE INVENTION

An embodiment of the present invention includes a method for the engraving of channels using either 3D printing (3DP), laser micromachining (LMM) or milling micromachining (MMM) on a polymer substrate. In embodiments of the method, each of the previously mentioned rapid prototyping methods is utilized in a step-wise lamination process to generate micro- or milli-fluidic devices. In embodiments, the engraved parts are thermally bonded with double-sided commercially available adhesive tape (Pyralux FRO 100) that has excellent solvent compatibility and has been laser micromachined through its whole thickness. In one instance of this embodiment, the channel height is governed by the thickness of the adhesive tape which is bonded between an upper and lower part with cut through guiding holes in the corners and fluid inlets/outlet in the upper part. In another instance of this embodiment, adhesive tape with the minimum available thickness (5 μm) is used and the channel height is mainly governed by the depth of the engraved features using 3DP and micromachining methods. This hybrid rapid prototyping method allows the expansion of the achieved feature sizes that would be normally achieved with 3DP of monolithic fluidic devices. In addition, the claimed method allows the fabrication of 3D heterogeneous devices both with respect to the feature sizes (variable emulsification) and to the material properties (chemically or non-chemically resistant devices) in spaces without clean-room environment conditions.

In exemplary implementations of this invention the rapid prototyped emulsifiers made either from different materials (chemically or non-chemically inert) and/or with varying geometrical feature sizes (channel height or width) can be assembled through subsequent stacking and bonding into a Variable Emulsifier (VE) to optimize the mass-production of monodispersed particles of desired size and allowing stable scaleup continuous production.

An embodiment of the present invention includes a method for screening for optimal bioavailability. In embodiments of this method, a USB microscope camera with an appropriate resolution at a specific field of view is interfaced with a computer using the Open CV computer vision library. The camera is mounted vertically above the VE right after the outlet and performs particle detection and segmentation. Both image processing tasks are automated and optimized based on the ambient light conditions allowing objective particle segmentation using image processing filtering algorithms that aim to extract the outline of the passing particles and the quantification of size metrics. The camera sends a feedback signal to a control loop, where the quantified particle size metric is compared real-time with the desired particle size and the syringes are appropriately actuated to tune the ratio of the volumetric flow rate of the continuous fluid phase over the volumetric flow rate of the dispersed fluid phase (API) to return to optimal conditions without stopping the operation.

There is a transient multiphysics model for virtual (in silico) testing of the VE. allowing the discovery of optimal conditions for desired particle size distributions upon changes in the single emulsifier geometrical feature sizes, the configuration of the single emulsifiers in the VE tower, flow rate settings and physicochemical parameters of the API and solvents.

In exemplary implementations of this invention the VE is configured to discover the optimal conditions for desired particle size distributions upon changes in the operating environment or the API, solvents or other physicochemical parameters of the feedstock.

In exemplary implementations of this invention the VE is configured for portable operation.

In exemplary implementations of this invention the VE is configured to create a range of flowrate settings to create a range of particle size distributions to create a test set for bioavailability, stability, injectability etc. assays.

In exemplary implementations of this invention the VE allows for the offgassing of volatile solvents into the open air without the need for integrated vacuum systems.

In exemplary implementations of this invention, an optical feedback loop controls relative flows of the solvent, antisolvent and API to discover the optimal settings such that the resultant particles are of the desired characteristics such as size and dispersion width.

The VE performs this automated condition discovery in varying outside environments and is agnostic to the actual nature of the materials being used.

Further, the VE can perform this task without using environmental inputs, for instance variations in atmospheric temperature, relative humidity and atmospheric pressure which are known to affect the extraction of the solvent, do not need to be explicitly measured or monitored because the feedback loop system only depends on the user's defined desired outcome.

Embodiments of the invention disclosed herein include one or more methods that can be integrated to implement droplet-based manufacturing of drugs. The methods can be implemented under known paradigms, or may be integrated to implement new paradigms or approaches to droplet-based drug manufacturing.

BRIEF DESCRIPTION OF THE DRAWINGS

FIG. 1 is a set of exploded views illustrating the hybrid rapid prototyping of single emulsifiers.

FIG. 2 is a set of exploded views illustrating the stacking of the previously rapid prototyped single emulsifiers of the same or varying material properties or dimensions into a Variable Emulsifier (VE) tower for the mass production of emulsions.

FIG. 3A is a perspective view of an aluminum encasing that allows the flow control of the VE tower.

FIG. 3B is a cutaway view of the design of FIG. 3A illustrating the aluminum encasing that allows the flow control of the VE tower.

FIG. 3C is an exploded view of the cutaway view of FIG. 3B illustrating the aluminum encasing that allows the flow control of the VE tower.

FIG. 4 is a collection of views illustrating the concept of a VE for the production of emulsions of varying sizes through channels of varying characteristic dimensions.

FIG. 5 is a stylized flow schematic including time-based results of the multiphase flow model in a single emulsifier.

FIG. 6 is a control system block diagram illustrating the in-process quality control strategy for optimal production of emulsions with low dispersion or other optical properties.

DETAILED DESCRIPTION OF THE PREFERRED EMBODIMENTS

The Variable Emulsifier (VE) of the preferred embodiment consists of 3 microfluidic components 1. Manifolds
2. Resistors
3. Flow Generators with varying nozzle sizes Geometry allows for a 1-step process to produce monodisperse emulsions of varying sizes and may be used to rapidly screen for optimal size for maximal bioavailability of API particles either on lab bench for in vivo dissolution or in vitro animal studies, and potentially even patient-specific handhelds for maximal drug inhalation for respiratory applications.

Across Borders for Legal Compliance

The apparatus powered by portable battery and configured in a self-contained carrying case can be used to comply with country specific drug manufacturing laws.

Local Just in Time Production Compliance

The apparatus powered by portable battery and configured in a self-contained carrying case can be used to defeat the problems with cold supply chain.

Outside of pharmaceuticals, the technology can be used to rapidly produce colloids of varying sizes and is useful for quantum dot production, electronics, photodynamic therapy, therapeutic agent delivery, sensors, probes, diagnostics, and catalysis.

For a more complete understanding of the present invention, reference is made to the following detailed description of an exemplary embodiment considered in conjunction with the accompanying figures, in which:

FIG. 1 is a set of exploded views 100 illustrating the hybrid rapid prototyping of single emulsifiers, whose characteristic dimensions (channel height) is governed by the thickness of the adhesive tape (A-B) or the by the engraved depth in chemically or non-chemically inert materials using micromachining methods (C-D). In particular:

Item 102 (A) shows the hybrid rapid prototyping of a single emulsifier whose characteristic dimensions (channel height) is governed by the thickness of the adhesive tape 104. A type of adhesive tape 104 can be DuPont™ Pyralux Adhesive FRO 100. Items 106 and 108 are developed by 3D printing (3DP) and are made of 3DP Resin. Depicted is an engraved channel 103 on the adhesive tape 104, and guiding apertures 107 for inlet ports and an outlet.

Item 112 (B) shows the hybrid rapid prototyping of a single emulsifier whose characteristic dimensions (channel height) is governed by the thickness of the adhesive tape 114. A type of adhesive tape 114 can be DuPont™ Pyralux Adhesive FRO 100. Items 116 and 118 are developed by milling micromachining and are made of FR4—a NEMA grade designation for glass-reinforced epoxy laminate material or Polyether ether ketone (PEEK). Depicted is an engraved channel 115 on the adhesive tape 114, and guiding apertures 117 for inlet ports and an outlet.

Item 122 (C) shows the hybrid rapid prototyping of a single emulsifier whose characteristic dimension (channel height) is governed by the engraved depth in chemically or non-chemically inert materials using micromachining methods. Item 124 is developed by laser micromachining, and contains an engraved channel 125. Items 126 and 128 are developed by 3D printing (3DP) and are made of 3DP Resin. Depicted are guiding apertures 127 for inlet ports and an outlet.

Item 132 (D) shows the hybrid rapid prototyping of a single emulsifier whose characteristic dimension (channel height) is governed by the engraved depth in chemically or non-chemically inert materials using micromachining methods. Item 134 is developed by laser micromachining, and contains an engraved channel 135. Items 136 and 138 are developed by milling micromachining and are made of FR4—a NEMA grade designation for glass-reinforced epoxy laminate material or Polyether ether ketone (PEEK). Also depicted are guiding apertures 137 for inlet ports and an outlet.

Figure 2B:
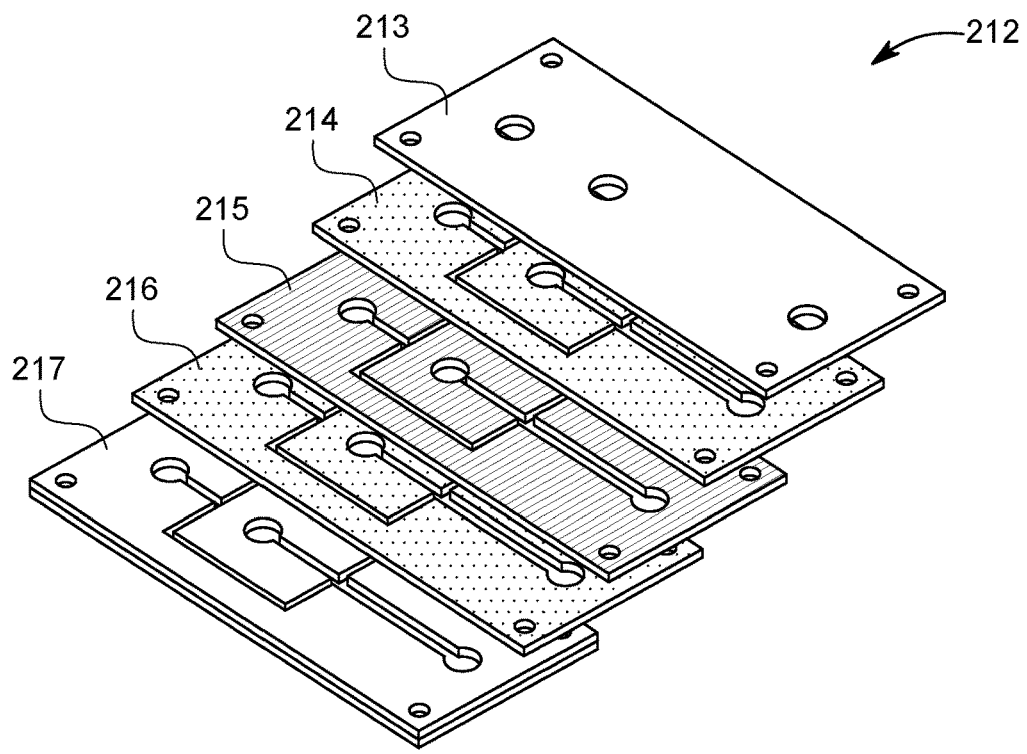
Figure 2C:
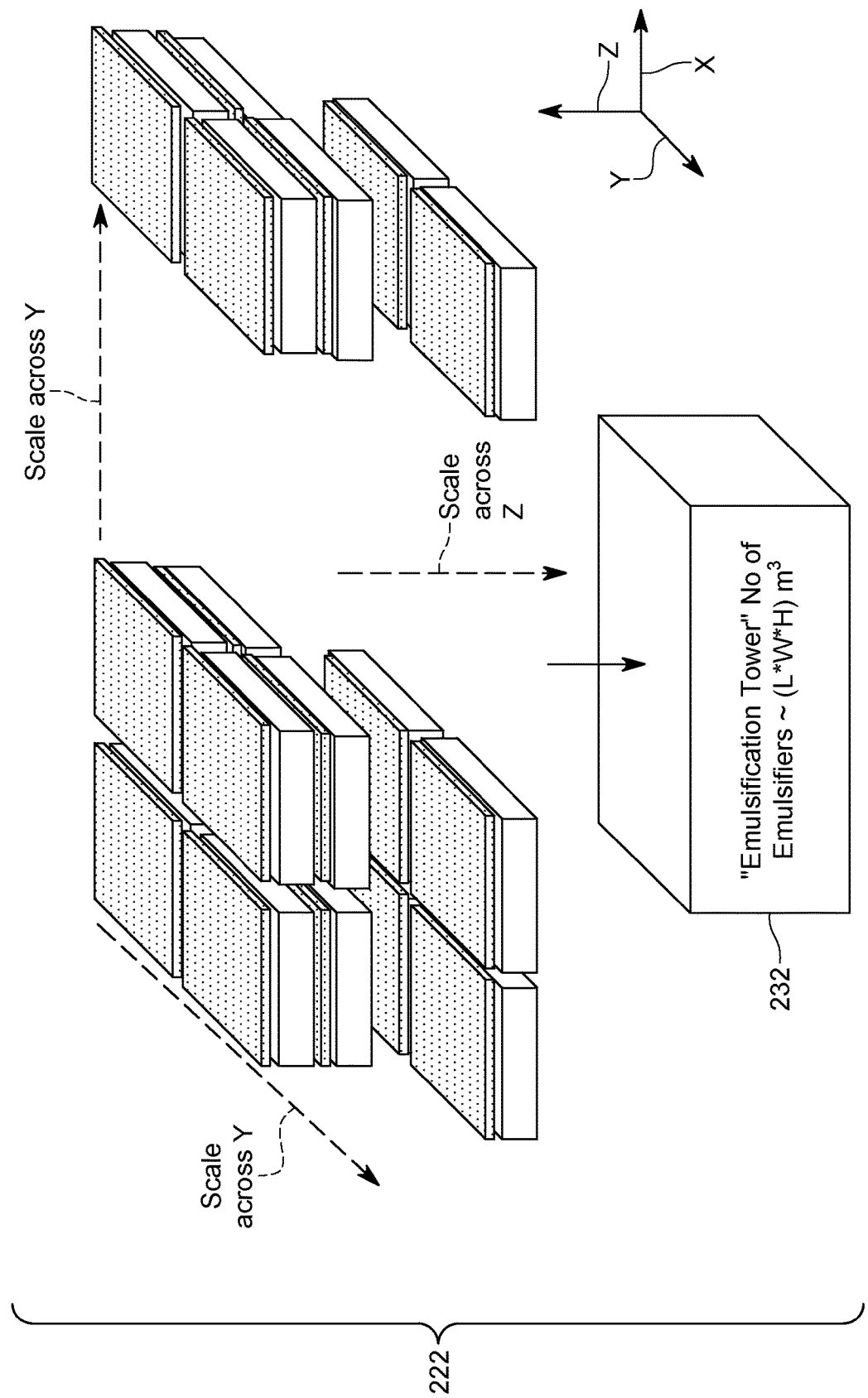

FIG. 2 is a set of exploded views illustrating the stacking of the previously rapid prototyped single emulsifiers of the same or varying material properties or dimensions into a Variable Emulsifier (VE) tower for the mass production of emulsions (A-B). Item 202 (A) is one of the prototyped single emulsifiers that make up the VE tower 232. Item 202 consists of 3D printed materials (203, 205, 207), and either adhesive or laser micromachining material (204, 206). Item 212 (B) is also one of the a prototyped single emulsifiers that make up the VE tower 232. Item 212 consists of 3D printed materials (213, 217), adhesive or laser micromachining material (214, 216), and milling micromachining material (215). The design allows the scaling up the emulsifiers number 222 with the volume of the VE tower 232. The scaling occurs across 3 dimensions X-Y-Z. The number of emulsifiers in the emulsification tower 232 can be approximated by length (L)*width (W)*height (H)*the cube of the mass (m), or $(L*W*H)m^3$.

Figure 3A:
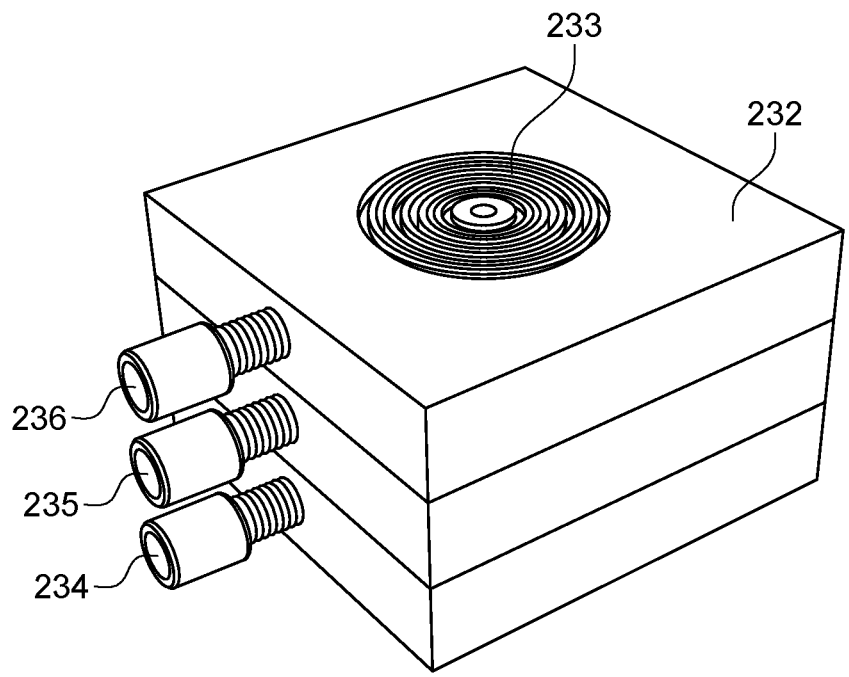

FIG. 3A is a perspective view illustrating an aluminum encasing 233 that allows the flow control of the VE tower 232 through single inlet ports (235 and 236) for the dispersed 235 and the continuous 236 phase and a single outlet port 234 for the collection of the produced emulsions.

Figure 3B:
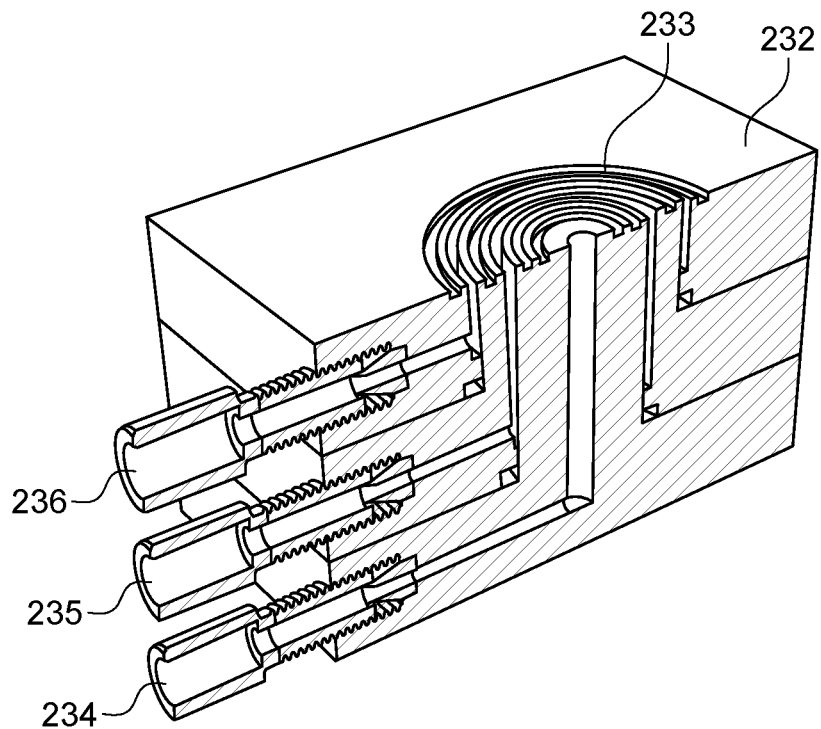

FIG. 3B is a cutaway view of the design of FIG. 3A illustrating the aluminum encasing 233 that allows the flow control of the VE tower 232 through single inlet ports (235 and 236) for the dispersed 235 and the continuous 236 phase and a single outlet port 234 for the collection of the produced emulsions.

Figure 3C:
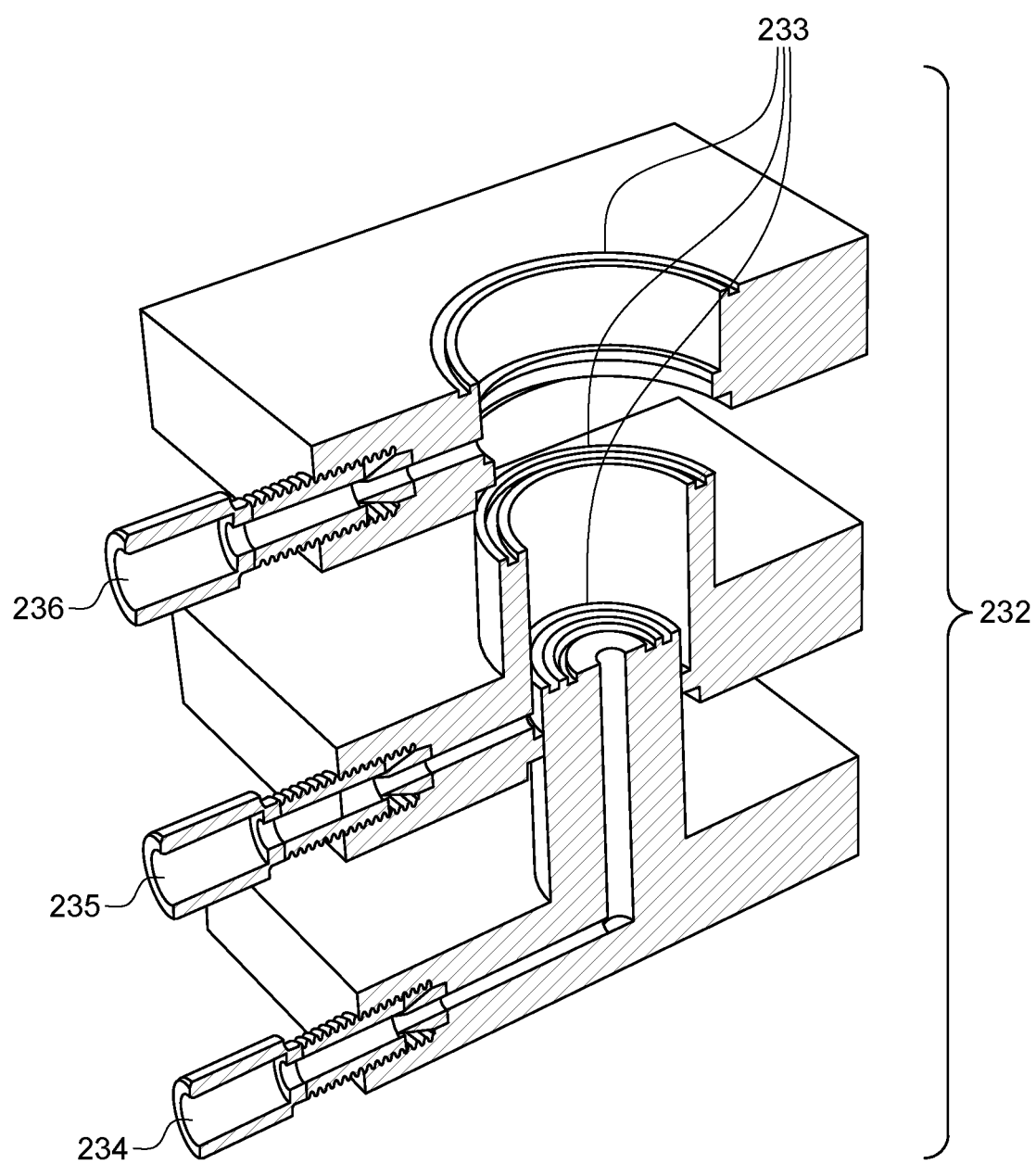
Figure 4A:
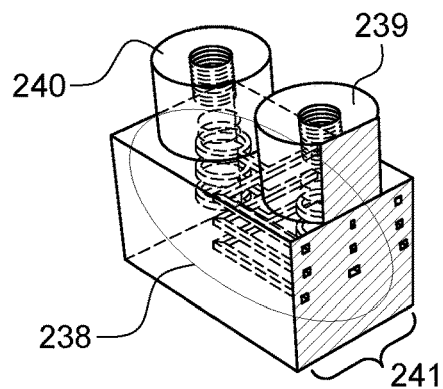
Figure 4B:
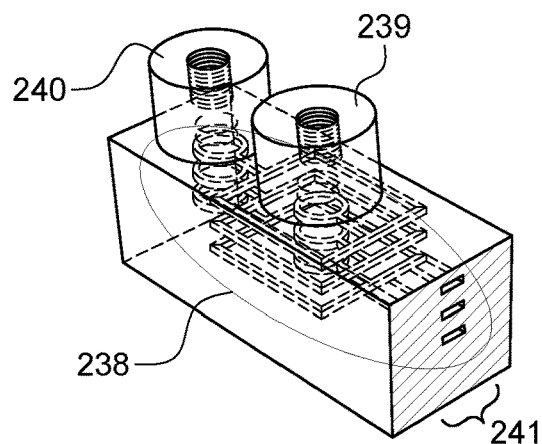
Figure 4C:
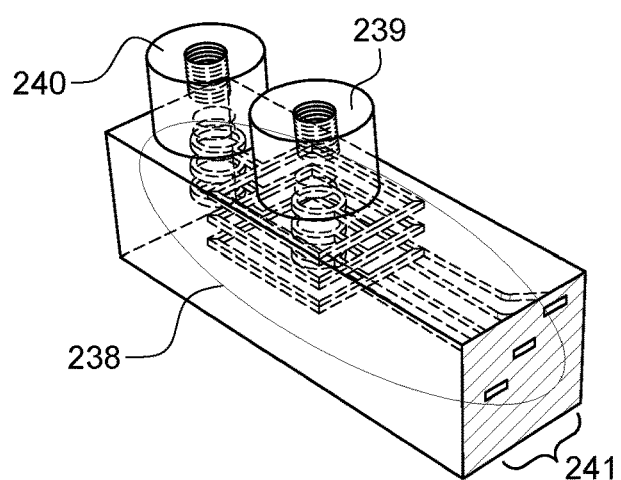
Figure 4D:
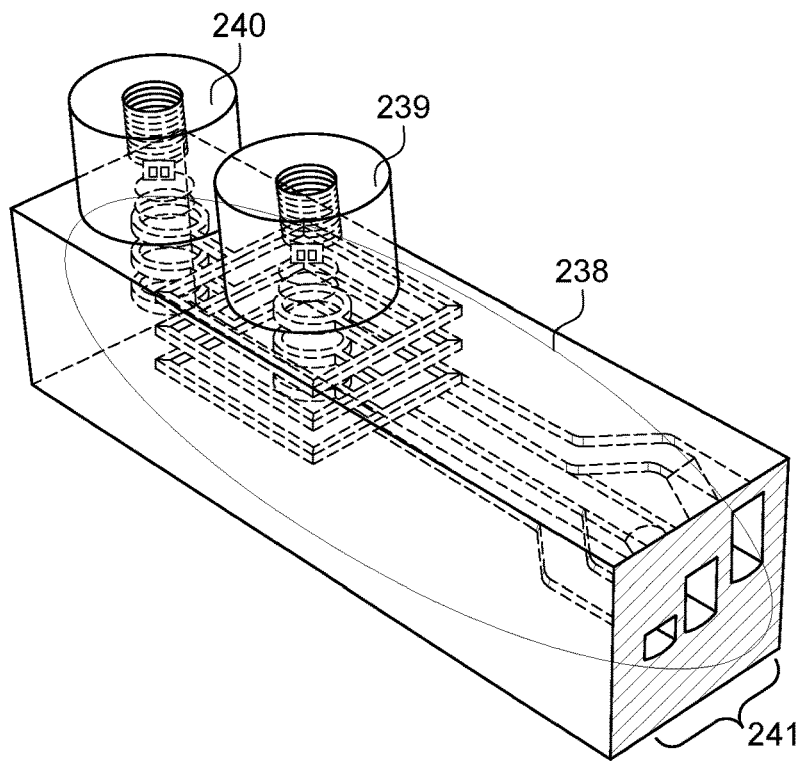
Figure 4E:
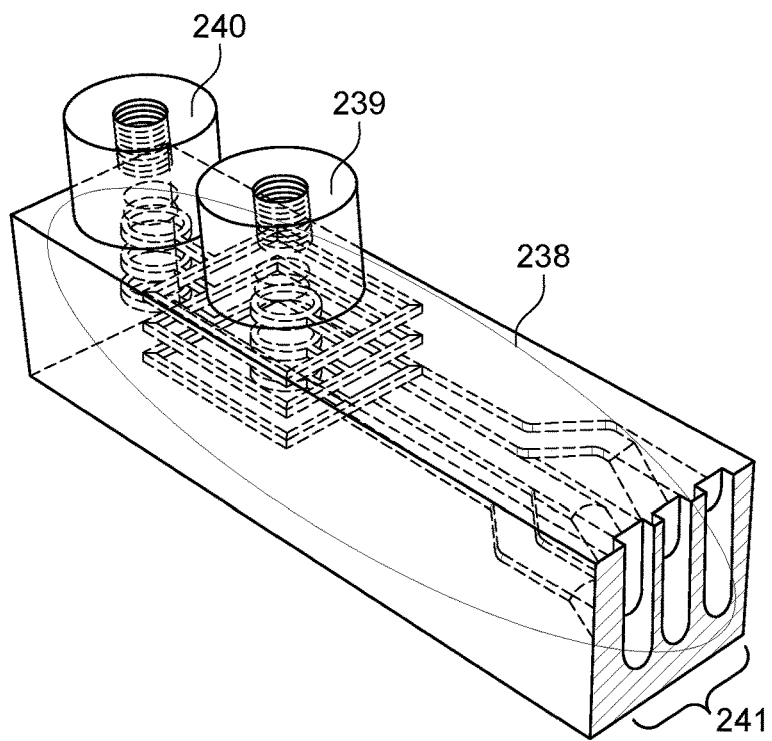
Figure 4F:
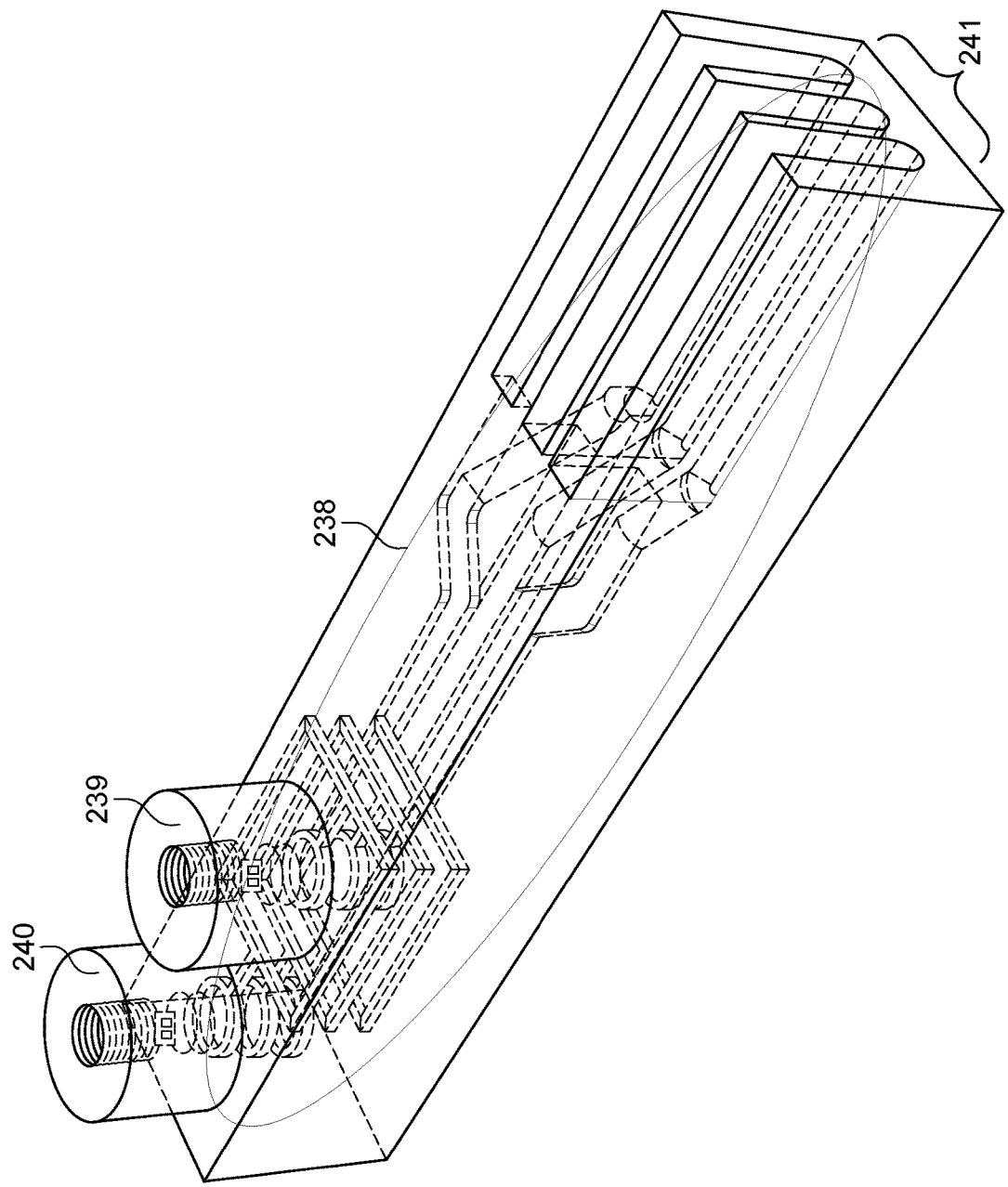
Figure 4G:
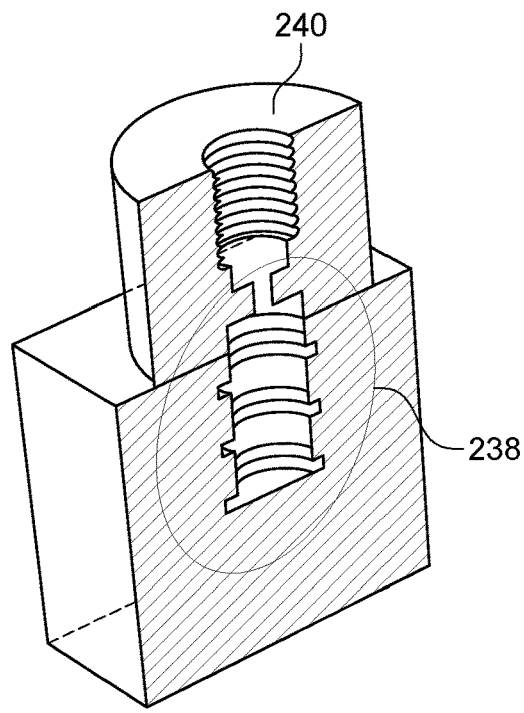
Figure 4H:
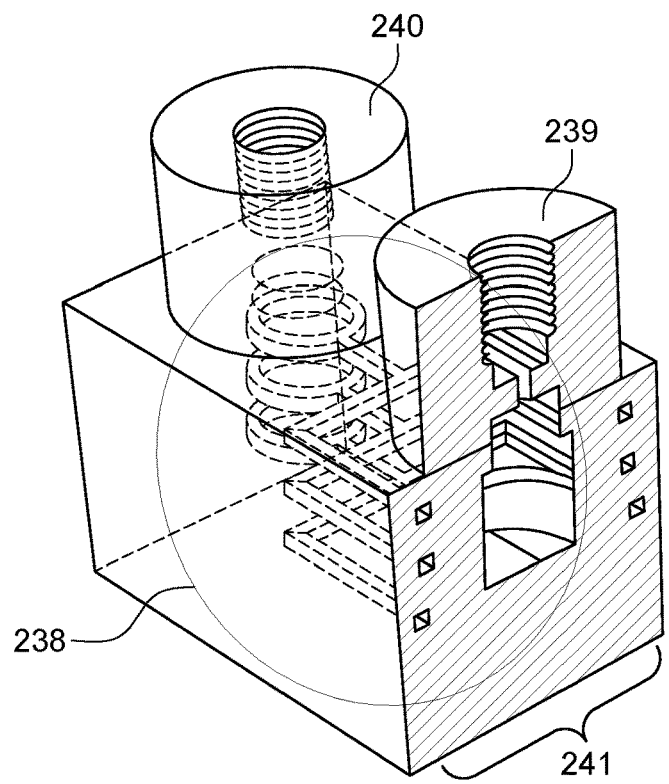

FIG. 3C is an exploded view of the cutaway view of FIG. 3B illustrating the aluminum encasing 233 that allows the flow control of the VE tower 232 through single inlet ports (235 and 236) for the dispersed 235 and the continuous 236 phase and a single outlet port 234 for the collection of the produced emulsions.

FIG. 4 is a collection of views illustrating the concept of a VE for the production of emulsions (a-f) of varying sizes through channels 238 of varying characteristic dimensions. As shown, each of the emulsifiers has a dispersed 239 and continuous 240 phase as well as outlet ports 241. Items g and h of FIG. 4 are cutaway views of an emulsifier with channels 238, and dispersed 239 and continuous 240 phases. The outlet ports 241 also have varying characteristic dimensions.

Figure 5:
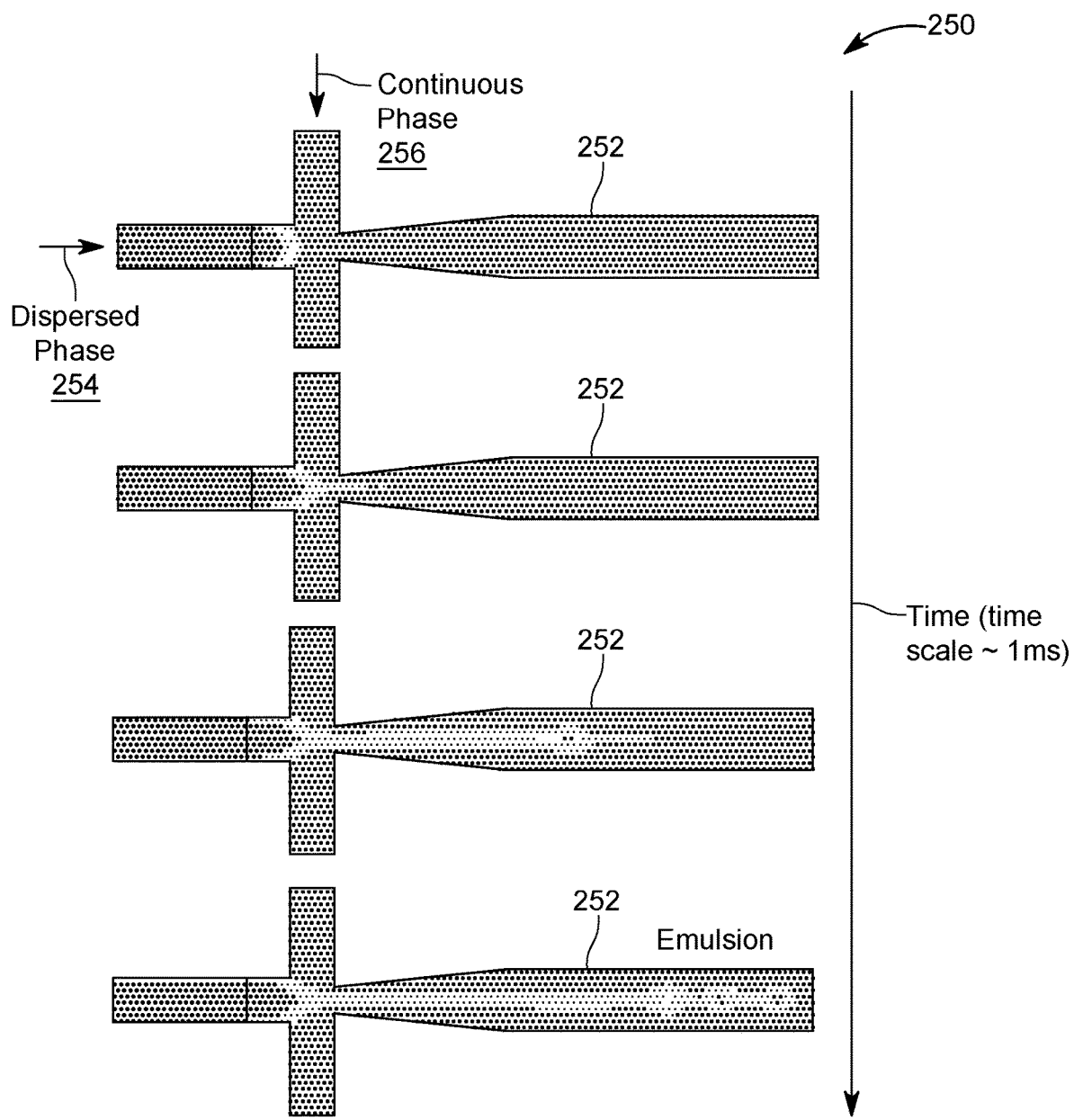

FIG. 5 is a stylized flow schematic including time-based results of the multiphase flow model 250 in a single emulsifier 252. The model 250 solves the fluid flow equations coupled with the level set equation which allows tracking of the interface between the dispersed 254 and the continuous phase 256. The model 250 can capture the fluid instability that occurs when flowing two immiscible fluids resulting to emulsification. The model's 250 execution time is approximately 1 millisecond (ms), scaled.

Figure 6:
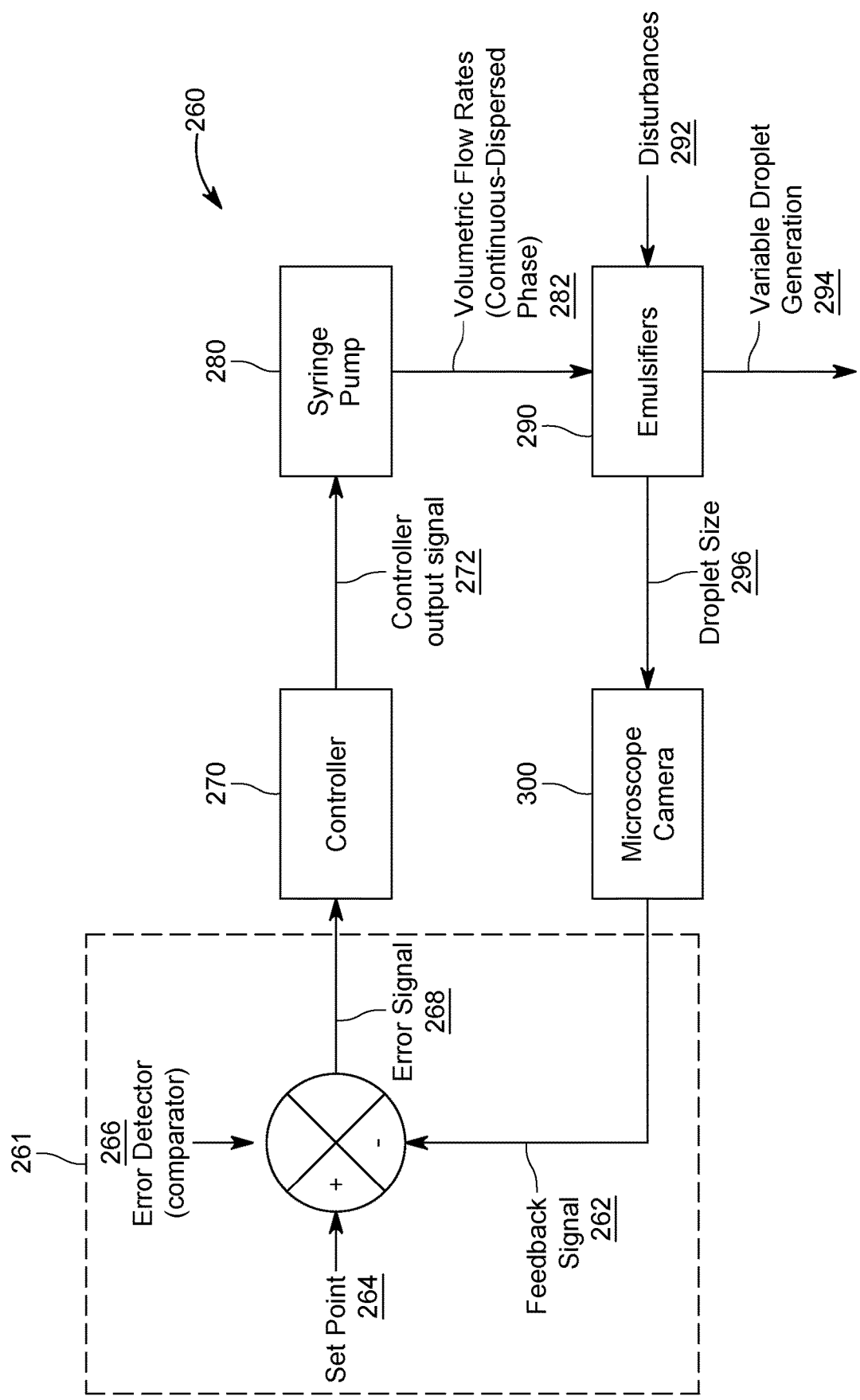

FIG. 6 is a control system block diagram illustrating the in-process quality control strategy 260 for optimal production of emulsions with low dispersion or other optical properties. The quality control system consists of an error detector 261, controller 270, syringe pump 280, the actual emulsifiers 290, and a microscope camera 300. A feedback signal 262 is received from the microscope camera 300 as input to a comparator 266 which compares the feedback signal 262 with a set point 264 representing the desired or target value for the process value of the emulsion production system. If the set point 264 is not met by the feedback signal 262, the comparator 266 sends an error signal 268 to the controller 270. Controller 270 continuously runs the comparator 266 to calculate the error signal 268, and can be implemented as a standard proportional-integral-derivative (PID) controller. Controller 270 sends an output signal 272 to the syringe pump 280 which administers fluid based on volumetric flow rates 282 to implement a continuous-dispersed phase to the emulsifiers 290. The control strategy 260 monitors disturbances 292 that happen to the emulsifiers 290 within the system. As a result of this process, emulsifiers 290 produce variable droplet generation 294 as a correction. The droplet size 296 parameter is input into the microscope camera 300, generating a feedback signal 262 to continue control strategy loop system 260. Detection of the disturbances 292 together with the overall in-process continuous and feedback enabled quality control system 260 can be implemented using computer vision methods, machine olfaction methods and/or in-situ characterization methods.

Principle Operation of VE Tower Topography Geometry

The principle of operation of the VE tower is based on two different topography geometry configurations that are depicted in FIGS. 3A-C and FIG. 4, respectively. Both configurations aim to provide efficient liquid transportation within the channels of the parallelized/stacked single emulsifiers with the use of only 2 inlet ports and 1 outlet port independently of the number of the single emulsifiers. All liquid operations are handled by two different user-controlled syringe pumps that control the volumetric flow rate of the supplied liquids (continuous and dispersed phase) through the 2 inlet ports.

In the first configuration, the VE tower and the liquid handling encasing system are separately fabricated. The liquid handling encasing system is depicted in FIGS. 3A-C. According to this configuration, the continuous phase liquid is provided through the inlet port 236 and the dispersed phase liquid is provided through the inlet port 235. Inlet ports 236 and 235 have a diameter at the order of mm. They communicate with channel 233, creating a pathway inward into the tower for the liquid. The channel has a diameter of the mm scale. It should preferably be sized as large as possible to minimize pressure disturbances that ultimately cause variations in the size of the emulsions. The VE tower configurations depicted in FIG. 1 and FIG. 2 are firmly attached on the liquid handling encasing system depicted in FIGS. 3A-C and the formed emulsions are collected at the outlet port 234.

In the second configuration depicted in FIG. 4, the VE tower and the liquid handling system are fabricated in a one step process. According to this configuration, the continuous phase liquid is provided through the inlet port 240 and the dispersed phase is provided through the inlet port 239. Inlet ports 240 and 239 have a diameter at the order of mm. They communicate with channels 238, creating a pathway inward into the tower for the liquid. The channel has a diameter of the mm scale. It should preferably be sized as large as possible to minimize pressure disturbances that ultimately cause variations in the size of the emulsions. Both liquids are distributed in each single emulsifier through channel 238 connecting the stacked single emulsifiers. The formed emulsions are collected at the outlet port 241 that has separate compartments connected to the fluidic channels of each single emulsifier.

It is to be understood that the embodiments described herein are merely exemplary and that a person of ordinary skill in the art may make many variations and modifications without departing from the spirit and scope of the invention. All such variations and modifications are intended to be included within the scope of the invention as disclosed.

What is claimed is:

1. An apparatus for formation of encapsulation emulsions from both of a continuous phase liquid and a dispersed phase liquid, comprising:
    a plurality of stacked rapidly prototyped single emulsifiers scaled across three dimensions to form a variable emulsifier tower, each single emulsifier comprising a plurality of channels, guiding holes, a continuous phase liquid inlet, a dispersed phase liquid inlet and an outlet, wherein the continuous phase liquid inlet and the dispersed phase liquid inlet lead to respective ones of the plurality of channels that meet at a point and intersect in fluid communication with one another, wherein an outlet channel continues past said point toward the outlet, whereby respective fluids when driven within the plurality of channels to meet at the point may collide while in-channel to create the encapsulation emulsion interior to the outlet channel prior to dispersal through the outlet; and
    a casing that houses the stack of emulsifiers, and allows flow control of the variable emulsifier tower through single inlet ports for a dispersed and continuous phase, and a single outlet port for collection of produced emulsions; further comprising a control system actuating liquid pressure into the continuous phase liquid inlet and the dispersed phase liquid inlet in response to an error signal derived from the size of an emulsion exiting the outlet, wherein the control system comprises a camera, a comparator, a controller and a pump, wherein: (i) the camera is configured to send an image of the emulsion to an image processing filtering algorithm that (1) extracts an outline of a passing emulsion particle, (2) quantifies the passing emulsion particle's size, and (3) sends said particle size to a comparator as a feedback signal; (ii) the comparator (1) compares said passing emulsion particle's size real-time with a desired particle size to calculate an error signal, and (2) sends said error signal to a controller; and (iii) the controller creates an output signal to the pump to adjust a volumetric flow rate based on the error signal to return a subsequent passing emulsion particle to optimal conditions without stopping operation.

2. The apparatus of claim 1, wherein the single emulsifiers are manufactured by a method comprising:
    engraving the channels on an upper part polymer substrate and a lower part polymer substrate;
    engraving the guiding holes on the upper part polymer substrate and a lower part polymer substrate; and
    thermally bonding the engraved channels with an adhesive tape that has been laser or otherwise machined though the whole thickness of the adhesive tape to form an emulsifier.

3. The apparatus of claim 2, wherein the upper part and lower part are developed by 3D printing and comprise 3D printed resin.

4. The apparatus of claim 2, wherein the upper part and lower part are manufactured by milling micromachining and comprise FR4 or polyether ether ketone.

5. The apparatus of claim 2, wherein a height of the engraved channels depends on the thickness of the adhesive tape.

6. The apparatus of claim 2, wherein a height of the engraved channels depends on a micromachining method used to engrave the channels within chemically or non-chemically inert materials.

7. The apparatus of claim 1, wherein the variable emulsifier tower is powered by a portable battery and configured in a self-contained carrying case.

8. The apparatus of claim 1, wherein each emulsion is an encapsulation of a hydrophilic active ingredient.

9. The apparatus of claim 1, wherein each emulsion is a drug.

10. A method of manufacturing a variable emulsifier tower used for the mass production of emulsions of various sizes, comprising:
    stacking a plurality of rapidly prototyped single emulsifiers scaled across three dimensions to form the variable emulsifier tower, wherein each single emulsifier comprises a plurality of channels, guiding holes, a continuous phase liquid inlet, a dispersed phase liquid inlet and an outlet; and
    enclosing the stack with a casing, wherein the casing allows flow control of the variable emulsifier tower through single inlet ports for a dispersed and continuous phase and a single outlet port for collection of produced emulsions; and
    provisioning a control system actuating liquid pressure into the continuous phase liquid inlet and the dispersed phase liquid inlet in response to an error signal derived from the size of an emulsion exiting the outlet, wherein the control system comprises a camera, a comparator, a controller and a pump, wherein: (i) the camera is configured to send an image of the emulsion to an image processing filtering algorithm that (1) extracts an outline of a passing emulsion particle, (2) quantifies the passing emulsion particle's size, and (3) sends said particle size to a comparator as a feedback signal; (ii) the comparator (1) compares said passing emulsion particle's size real-time with a desired particle size to calculate an error signal, and (2) sends said error signal to a controller; and (iii) the controller creates an output signal to the pump to adjust a volumetric flow rate based on the error signal to return a subsequent passing emulsion particle to optimal conditions without stopping operation.

11. The method of claim 10, wherein the single emulsifiers are manufactured by a method comprising:
- engraving channels on an upper part polymer substrate and a lower part polymer substrate;
- engraving guiding holes on the upper part polymer substrate and a lower part polymer substrate; and
- thermally bonding the engraved channels with an adhesive tape that has been laser micromachined though a whole thickness of the adhesive tape to form an emulsifier.

12. The method of claim 11, wherein the upper part and lower part are developed by 3D printing and comprise 3D printed resin.

13. The method of claim 11, wherein the upper part and lower part are manufactured by milling micromachining and comprise FR4 or polyether ether ketone.

14. The method of claim 11, wherein a height of the engraved channels depends on the thickness of the adhesive tape.

15. The method of claim 11, wherein a height of the engraved channels depends on a micromachining method used to engrave the channels within chemically or non-chemically inert materials.

16. The method of claim 10, further comprising providing a means for tracking an interface between the dispersed and continuous phase by capturing a fluid instability that occurs when flowing two immiscible fluids resulting to emulsification, wherein the means solves fluid flow equations and a level set equation.

17. The method of claim 10, further comprising providing a portable battery to provide power to the variable emulsifier tower and a carrying case to contain the variable emulsifier tower.

18. The method of claim 10, wherein each emulsion is an encapsulation of a hydrophilic active ingredient.

19. The method of claim 10, wherein each emulsion is a drug.

20. The method of claim 10, further comprising using the variable emulsifier tower to optimize the mass production of monodispersed particles of desired size to allow stable scaleup continuous production.

21. The method of claim 10, further comprising using the variable emulsifier tower to rapidly screen for optimal size and maximal bioavailability of active pharmaceutical ingredient particles.

22. The method of claim 10, further comprising using the variable emulsifier tower to produce patient-specific handhelds for maximal drug inhalation for respiratory applications.

23. The method of claim 10, further comprising configuring the variable emulsifier tower to discover the optimal conditions for desired particle size distributions upon changes in an operating environment or an active pharmaceutical ingredient, solvents or other physicochemical parameters of a feedstock.

24. The method of claim 10, further comprising configuring the variable emulsifier tower to create a range of flowrate settings to create a range of particle size distributions to create a test set for bioavailability assays, stability assays, and injectability assays.

25. The method of claim 10, wherein the variable emulsifier tower allows for the offgassing of volatile solvents into the open air without the need for integrated vacuum systems.

* * * * *